US005198458A

United States Patent [19]

[11] Patent Number: 5,198,458

[45] Date of Patent: Mar. 30, 1993

Higuchi et al.

[54] PYRROLIDINEAMIDE DERIVATIVES OF ACYLAMINO ACID AND PHARMACEUTICAL COMPOSITION CONTAINING THE SAME

[75] Inventors: Naoki Higuchi; Masayuki Saitoh; Masaki Hashimoto, all of Osaka; Harukazu Fukami, Kyoto; Takaharu Tanaka, Osaka, all of Japan

[73] Assignee: Suntory Limited, Osaka, Japan

[21] Appl. No.: 638,148

[22] Filed: Jan. 9, 1991

Related U.S. Application Data

[63] Continuation of application Ser. No. 224,859, Sep. 15, 1988, now abandoned, which is a division of application Ser. No. 010,490, Feb. 3, 1987, now U.S. Pat. No. 4,826,870.

[30] Foreign Application Priority Data

Feb. 4, 1986 [JP] Japan .................................. 61-22756
Feb. 28, 1986 [JP] Japan .................................. 61-43821

[51] Int. Cl.[5] .................... A61K 31/40; C07D 295/104

[52] U.S. Cl. .................................... 514/397; 514/414; 514/423; 548/468; 548/540; 548/314.7

[58] Field of Search ........................ 548/540, 468, 336; 514/423, 397, 414

[56] References Cited

U.S. PATENT DOCUMENTS

| | | | |
|---|---|---|---|
| 4,077,951 | 5/1978 | Loffet | 260/112.5 R |
| 4,701,465 | 10/1987 | Tanaka et al. | 514/423 |
| 4,743,616 | 5/1988 | Tanaka et al. | 514/423 |
| 4,757,083 | 7/1988 | Higuchi et al. | 514/423 |
| 4,772,587 | 9/1988 | Tanaka et al. | 514/423 X |
| 4,826,870 | 5/1989 | Higuchi et al. | 548/540 X |

FOREIGN PATENT DOCUMENTS

| | | |
|---|---|---|
| 0046707 | 3/1982 | European Pat. Off. . |
| 0254545 | 1/1988 | European Pat. Off. . |
| 60-172929 | 9/1985 | Japan . |
| 60-188317 | 9/1985 | Japan . |
| 1467927 | 3/1977 | United Kingdom . |

OTHER PUBLICATIONS

Proceedings of the 1984 Annual Meeting of "The Agricultural Chemical Society" of Japan, pp. 752–754 (1984).

Yoshimoto, et al., Agric. Biol. Chem., 42 (No. 12), pp. 2417–2419 (1978).

Merck Index, p. 35, CA 195 and CA 196 (date not known).

*Primary Examiner*—Joseph Paul Brust
*Attorney, Agent, or Firm*—Cushman, Darby & Cushman

[57] ABSTRACT

A compound of the general formula:

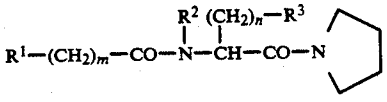

(1)

wherein m is an integer of 1 to 7, n is 0 or an integer of 1 to 5, $R^1$ is the phenyl, a substituted phenyl, the phenoxy, a substituted phenoxy or a saturated or unsaturated straight alkyl having 5 to 18 carbon atoms, $R^2$ is hydrogen atom, $R^3$ is hydrogen atom, a branched or unbranched alkyl having 3 to 5 carbon atoms, the phenyl, hydroxyphenyl, benzyloxyphenyl, an alkylthio having 1 to 3 carbon atoms in its alkyl moiety, amino, carboxyl, hydroxy, benzyloxy, indolyl or imidazolyl, or $R^2$ and $R^3$ together form a single bond between the carbon atom and the nitrogen atom, and a pharmaceutical composition containing said compound are provided. The compound is effective in curing amnesia because of its anti-prolyl endopeptidase activity.

4 Claims, No Drawings

PYRROLIDINEAMIDE DERIVATIVES OF ACYLAMINO ACID AND PHARMACEUTICAL COMPOSITION CONTAINING THE SAME

This is a continuation of application Ser. No. 07/244,859, filed Sep. 15, 1988, now abandoned, which is a division of application Ser. No. 07/010,490, filed Feb. 3, 1987, now U.S. Pat. No. 4,826,870.

FIELD OF THE INVENTION

The present invention relates to a pyrrolidineamide derivative of acylamino acid of the general formula (1):

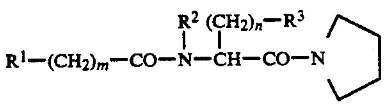

(1)

wherein m is an integer of 1 to 7, n is 0 or an integer of 1 to 5, $R^1$ is the phenyl, a substituted phenyl, the phenoxy, a substituted phenoxy or a saturated or unsaturated straight alkyl having 5 to 18 carbon atoms, $R^2$ is hydrogen atom, $R^3$ is hydrogen atom, a branched or unbranched alkyl having 3 to 5 carbon atoms, the phenyl, hydroxyphenyl, benzyloxyphenyl, an alkylthio having 1 to 3 carbon atoms in its alkyl moiety, amino, carboxyl, hydroxy, benzyloxy, indolyl or imidazolyl, or $R^2$ and $R^3$ together form a single bond between the carbon atom and the nitrogen atom; and a pharmaceutical composition containing said derivative.

More particularly, the compounds of the invention not only exhibit enzyme inhibiting activities against prolyl endopeptidase, but are also effective for the treatment and remedy of symptoms caused by organic disorders of the brain.

The term "organic disorders of the brain" here means various symptoms caused by ischemic disorders such as sequela of cerebral infarction, sequela of cerebral hemorrhage and sequela of cerebral arteriosclerosis, and various organic disorders caused by presbyophrenia, presenile dementia, amnesia, sequela of external head wounds, and sequela of cerebral operations.

Prolyl endopeptidase is known to inactivate neurotransmitters such as substance P, thyrotropin-releasing hormone (TRH) and neurotensin, or vasopressin speculatively associated with memory. Tsuru and Yoshimoto of the Department of Pharmaceutical Sciences, Nagasaki University, found that compounds capable of inhibiting prolyl endopeptidase activity were effective in preventing experimental amnesia caused in rats by scopolamine and suspected the influence of prolyl endopeptidase on the formation of memory. Based on this discovery, they suggested the potential use of antiprolyl endopeptidase substances as anti-amnesic agents.

A brain cell retains an intracellular environment completely different from the surrounding environment (extracellular liquid) and lives while maintaining this difference, which requires energy to be continually produced and supplied to the cell. Most of the energy necessary for nerve cells of the brain is supplied by oxygen and glucose which are constantly supplied from the blood, since these energy sources are not stored in the brain.

If there is a disorder in the brain, and the supply of oxygen and glucose is interrupted, then energy metabolic disorders will sequentially progress and the cells will lose their functions after a time, finally causing organic collapse, and failure of normal functions.

To prevent this, brain blood vessels themselves have developed mechanisms for controlling the bloodstream so as to safely supply the energy sources for the brain tissue and maintain a constant external environment for the cranial nerve cells.

When disorders of a blood vessel in the brain are internally treated, various kinds of brain circulation improving agents, brain vasodilators, brain metabolism improving agents and the like are used. In the present state of the art, however, these agents can ameliorate subjective symptoms but can only slightly relieve symptoms related to the nerves.

DESCRIPTION OF THE PRIOR ART

The U.S. patent specifications under Ser. No. 760,411 (filed on Jul. 30, 1985), now U.S. Pat. No. 4,743,616; Ser. No. 852,709 (filed on Apr. 16, 1986), now U.S. Pat. No. 4,772,587; Ser. No. 852,710 (filed on Apr. 16, 1986) now U.S. Pat. No. 4,873,342 and Ser. No. 852,711 (filed on Apr. 16, 1986), now U.S. Pat. No. 4,701,465, and the U.S. patent application entitled "Novel pyrrolidinylamide ester derivative having anti-prolyl endopeptidase activity and synthesis and use thereof" filed on Nov. 28, 1986, all of which have been assigned to the assignee of this invention, disclose certain types of compounds which have inhibitory activity against prolyl endopeptidase and are thus effective in treating amnesia.

SUMMARY OF THE INVENTION

An object of the present invention is to provide novel compounds that exhibit anti-amnesic effect because of their inhibitory activity against prolyl endopeptidase which is closely related to the treatment or curing of disorders caused by the various malfunctions of the brain mentioned above.

Another object of the invention is to provide novel compounds which possess the above-mentioned effects while displaying satisfactorily low toxicity levels by synthesis of novel compounds with structures which are similar to certain naturally occurring compounds from a combination of starting materials selected from fatty acids and amino acids or peptides which are highly safe natural substances.

A further object of the invention is to provide a pharmaceutical composition which contains said novel compounds and is especially effective in the treatment or curing of amnesia.

DETAILED DESCRIPTION OF THE PREFERRED EMBODIMENT

The present inventors have found that novel pyrrolidineamide derivatives of acylamino acid of the foregoing general formula (1) have anti-prolyl endopeptidase activity. They have also found that these novel compounds have anti-amnesic effects against animals suffering from experimental amnesia.

Thus the novel pyrrolidineamide derivatives of acylamino acid of the general formula (1) are effective in treating and curing mental disorders due to organic disorders of the brain, especially amnesia. The compounds of the formula (1) differ greatly from the known anti-amnesic agents of piracetam derivatives in that the former contains an amino acid residue and an acyl group. Because they are derivatives of amino acids, the compounds of the formula (1) exhibit extremely low levels of toxicity in organisms.

The amino acid residue in the compound of the invention may be derived from the group consisting of L-proline, L-glycine, L-alanine, L-valine, L-norvaline, L-leucine, L-norleucine, L-serine, L-homoserine, L-methionine, L-phenylalanine, L-tyrosine, L-aspartic acid, L-glutamic acid, L-lysine, L-arginine, L-histidine, L-tryptophane and derivatives thereof.

The compounds of the present invention may be produced by various known methods of peptide synthesis, but the compounds may advantageously be synthesized by the following methods of the inventors as explained hereunder. The abbreviations used herein represent the following meanings:

WSCD: N-ethyl-N',N'-dimethylaminopropylcarbodiimide

TEA: triethylamine

TFA: trifluoroacetic acid

As the first step, a carbonyl halide or a carboxylic anhydride of the general formula (2) or (2'):

$$R^1-(CH_2)_m-COX \quad (2)$$

$$[R^1-(CH_2)_m-CO]_2O \quad (2')$$

wherein $R^1$ and m have the meanings given above, and X is a halogen atom, is reacted with an amino acid of the general formula (3):

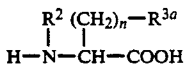
(3)

wherein $R^2$ is hydrogen atom, n is 0 or an integer of 1 to 5, $R^{3a}$ is hydrogen atom, a branched or unbranched alkyl having 3 to 5 carbon atoms, the phenyl, hydroxyphenyl, benzyloxyphenyl, an alkylthio having 1 to 3 carbon atoms in its alkyl moiety, benzyloxycarbonylamino, benzyloxycarbonyl, benzyloxy, indolyl or imidazolyl, or $R^2$ and $R^{3a}$ together form a single bond between the carbon atom and the nitrogen atom, optionally in the presence of a base, and the resulting product is then condensed with pyrrolidine to obtain a pyrrolidineamide derivative of acylamino acid of the present invention which has the general formula (1a):

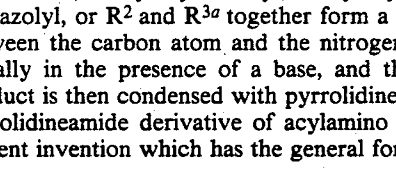
(1a)

wherein m, n, $R^1$, $R^2$ and $R^{3a}$ have the meanings given above.

The bases employable in this reaction include alkaline metal carbonates, trialkyl amines and aromatic amines. The reaction is preferably carried out below room temperature using a suitable solvent capable of dissolving said bases.

The condensation agents employable in the condensation with pyrrolidine include those conventionally used in peptide synthesis such as N,N'-dicyclohexylcarbodiimide, WSCD etc., as well as those commonly used in the acid chloride method, the combined anhydrides method, and the active ester method.

The protective group of hydroxyl group, amino group or carboxyl group in the compound (1a) can be removed easily by a conventional method. The de-protection is preferably conducted by catalytic reduction when the protective group is benzylether, benzylester, or by acid treatment when the protective group is benzyloxycarbonyl. The acids used in this de-protection may be selected from, for example, trifluoroacetic acid, hydrochloric acid, hydrofluoric acid and hydrobromic acid. Such de-protection of the corresponding compounds of the formula (1a) will result in the inventive compounds of the general formula (1b):

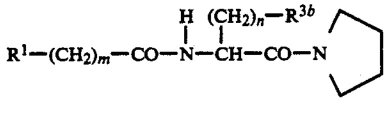
(1b)

wherein $R^1$, m and n have the meanings given above, and $R^{3b}$ is hydroxyphenyl, amino, carboxyl or hydroxy.

The novel compounds of the general formula (1) may also be produced from corresponding amino acids or derivatives thereof by treating said amino acids or derivatives with pyrrolidine to form pyrrolidineamides which are then acylated at the amino group.

The present invention is hereinunder described in greater detail by way of non-limiting examples.

EXAMPLE 1

N-[N-(γ-phenyl)butyryl-L-valyl]pyrrolidine

(Compound No. 1, SUAM 1252)

L-valine (10 mmol) was dissolved in 1N sodium hydroxide (20 ml) which was then diluted with water to give a volume of 30 ml. The resulting aqueous solution was slowly added dropwise under ice-cooling and stirring to a solution of γ-phenylbutyryl chloride (10 mmol) which had been previously dissolved in benzene (10 ml). Immediately thereafter an additional portion (10 ml) of 1N sodium hydroxide solution was added. After allowing the reaction mixture to return to room temperature, it was continuously stirred for one whole day and night.

After completion of the reaction, the mixture was extracted twice with ethyl ether to remove the unreacted acid chloride. The water phase was acidified by addition of hydrochloric acid. The resulting precipitate was extracted three times with ethyl acetate and the solvent was removed under vacuum, whereby N-(γ-phenyl)butyryl-L-valine was obtained. N-(γ-phenyl)butyryl-L-valine (1 equivalent) was then dissolved in dry methylene chloride (ca. 100 ml) together with pyrrolidine (1 equivalent), WSCD (1 equivalent) was added thereto and the mixture was continuously stirred at room temperature for one whole day and night. After the reaction the product had been washed successively with 1N hydrochloric acid, brine, saturated sodium bicarbonate and brine in that order, and had then been dried over anhydrous magnesium sulfate, the solvent was distilled off under vacuum and the residue was purified by column chromatography on silica gel, whereby the titled compound was obtained.

EXAMPLE 2

N-[N-(γ-phenyl)butyryl-L-prolyl]pyrrolidine (Compound No. 18, SUAM 1221)

L-proline (10 mmol) was dissolved in 1N sodium hydroxide (20 ml) which was then diluted with water to give a volume of 30 ml. The resulting aqueous solution was slowly added dropwise under ice-cooling an stirring to a solution of γ-phenylbutyryl chloride (10 mmol) which had been previously dissolved in benzene (10 ml). Immediately thereafter an additional portion (10 ml) of 1N sodium hydroxide solution was added. After allowing it to return to room temperature, the reaction mixture was continuously stirred for one whole day and night.

When the reaction was over, the mixture was extracted twice with ethyl ether to remove the unreacted acid chloride. The water phase was acidified by addition of hydrochloric acid. The resulting precipitate was extracted three times with ethyl acetate and the solvent was removed under vacuum, whereby N-(γ-phenyl)butyryl-L-proline was obtained. N-(γ-phenyl)butyryl-L-proline (1 equivalent) was then dissolved in dry methylene chloride (ca. 100 ml) together with pyrrolidine (1 equivalent), WSCD (1 equivalent) was added thereto and the mixture was continuously stirred at room temperature for one whole day and night. After the reaction, the product was washed successively with 1N hydrochloric acid, brine, saturated sodium bicarbonate and brine in that order and was then dried over anhydrous magnesium sulfate. The solvent was distilled off under vacuum and the residue was purified by column chromatography on silica gel, whereby the titled compound was obtained.

EXAMPLE 3

N-(N-oleoyl-L-prolyl)pyrrolidine (Compound No. 43, SUAM 1280)

L-prolylpyrrolidine (1 equivalent) and TEA (1 equivalent) were dissolved in dry tetrahydrofuran, and oleoyl chloride (1 equivalent) was added dropwise under cooling with ice. The mixture was stirred for 6 hours at room temperature and the hydrochloride salt of TEA which precipitated was removed by filtration. The solvent was distilled off under a reduced pressure, the residue was dissolved in a small volume of ether, the solution was successively washed with 1N hydrochloric acid, brine, saturated sodium bicarbonate and brine and the solution was then dried over anhydrous magnesium sulfate. The solution was concentrated under vacuum. An excess amount of diazomethane in ether was added to the residue to turn the unreacted oleic acid to its methyl ester. The residue which was obtained by distilling off the solvent under vacuum was subjected to medium pressure column chromatography on silica to obtain the titled compound as a pure oil.

EXAMPLE 4

N-{N-[γ-(m-phenoxyphenyl)butyryl]-L-prolyl}pyrrolidine (Compound No. 28, SUAM 1291)

γ-(m-Phenoxyphenyl) butyric acid (5 mmol) and L-proline methyl ester hydrochloride (5 mmol) were dissolved in dry methylene chloride (ca. 100 ml). An equimolar amount of triethylamine was added thereto followed by addition of WSCD (1.2 equivalent) and the mixture was continuously stirred at room temperature for one whole day and night. After the reaction was over, the mixture was washed successively with 1N hydrochloric acid, brine, saturated sodium bicarbonate and brine, the organic phase was dried over anhydrous sodium sulfate and the solvent was removed by distillation. Purification of the residue by way of column chromatography on silica gel resulted in n-[γ-(m-phenoxyphenyl}butyryl]-L-proline methyl ester. The product was dissolved in a small volume of methanol, to which 1N sodium hydroxide (100 ml) was then added and the whole mixture was stirred for 3 hours at room temperature. After the reaction was over, the resulting solution was acidified to about pH 2 by addition of 10N hydrochloric acid and then extracted with ethyl acetate. After the organic phase was dried over magnesium sulfate, the solvent was distilled off to obtain n-[γ-(m-phenoxyphenyl)butyryl]-L-proline. The n-[γ-(m-phenoxyphenyl)butyryl]-L-proline thus obtained (3 mmol) was dissolved with an equimolar amount of pyrrolidine in dry methylene chloride (ca. 100 ml), WSCD (1.2 equivalent) was added thereto and the mixture was continuously stirred at room temperature for one whole day and night. After the reaction was over, the resulting solution was successively washed with 1N hydrochloric acid, brine, saturated sodium bicarbonate and brine, the organic phase was dried over anhydrous sodium sulfate and the solvent was then distilled off. Purification of the residue by column chromatography on silica gel resulted in the N-{N-[γ-(m-phenoxyphenyl)butyryl]-L-prolyl}pyrrolidine aimed for.

EXAMPLE 5

N-{N-[γ(o-(E)-stilbenyloxy)butyryl]-L-prolyl)pyrrolidine (Compound No. 35, SUAM 1289)

o-Hydroxy-(E)-stilbene (10 mmol) and potassium hydroxide (15 mmol) were dissolved in dry dimethyl sulfoxide (ca. 10 ml), ethyl 4-bromobutyrate (11 mmol) was added there and the mixture was continuously stirred at room temperature for one whole day and night. After the reaction was over, the mixture was divided into water and benzene. The organic phase was dried over magnesium sulfate and the solvent was distilled off to obtain ethyl γ-(o-hydroxy-(E)-stilbenyloxy)butyrate. This product was dissolved in a small volume of methanol, 1N sodium hydroxide (ca. 100 ml) was added and the mixture was stirred for about 3 hours at room temperature. After the reaction was over, the resulting solution was acidified to about pH 2 by addition of 10N hydrochloric acid and then extracted with ethyl acetate. The organic phase was dried over magnesium sulfate and the solvent was distilled off to obtain γ-(o-(E)-stilbenyloxy)butyric acid. The resulting γ-(o-(E)-stilbenyloxy)butyric acid and L-proline methyl ester hydrochloride (5 mmol each) were dissolved in dry methylene chloride (ca. 100 ml), followed by the addition of an equimolar amount of triethylamine. WSCD (1.2 equivalent) was further added to the mixture which was then continuously stirred at room temperature for one whole day and night. After the reaction was over, the resulting solution was successively washed with 1N hydrochloric acid, brine, saturated sodium bicarbonate and brine, the organic phase was then dried over anhydrous sodium sulfate and the solvent was then distilled off. Purification of the residue by column chromatography on silica gel resulted in n-[γ-(o-(E)-stilbenyloxy)butyryl]-L-proline methyl ester. This product was dissolved in a small volume of methanol. 1N sodium hydroxide (ca 100 ml) was added thereto and the mixture was stirred for about 3 hours at room temperature. After the reaction was over, the resulting solution was acidified to about pH 2 by addition of 10N hydrochloric acid and was then extracted with ethyl acetate. After the organic phase had been dried over anhydrous magnesium sulfate, the solvent was distilled off to obtain n-[γ-(o-(E)-stilbenyloxy)-butyryl]-L-proline. The n-γ-(o-(E)-stilbenyloxy)-butyryl]-L-proline thus obtained (3 mmol) was dissolved with an equimolar amount of pyrrolidine in dry methylene chloride (ca. 100 ml), WSCD (1.2 equivalent) was added thereto and the mixture was continuously stirred at room temperature for one whole day and night. After the reaction was over, the resulting solution was successively washed with 1N hydrochloric acid, brine, saturated sodium bicarbonate and brine, the organic phase was dried over anhydrous sodium sulfate and the solvent was then distilled off. Purification of the residue by column chromatography on silica gel resulted in the titled compound.

The other compounds of the invention were obtained in a manner analogous to the foregoing examples. They are listed with their respective physical data in Table 1 and 2. Compounds Nos. 1, 3 and 4 were crystallized while all the other compounds were obtained in the form of oils.

TABLE 1
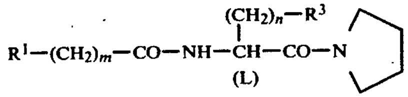
| Compound No. (SUAM No.) | $R^1-(CH_2)_m-$ | $-(CH_2)_n-R^3$ | IR Spectrum (film, $\nu$ $cm^{-1}$) | NMR Spectrum ($CDCl_3$, $\delta$ ppm) |
|---|---|---|---|---|
| 1 (1252) | 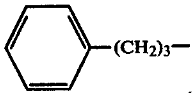 (m = 3) | $-CH(CH_3)_2$ (n = 0) | (KBr) 3240, 3050, 2950, 2870, 1655, 1620, 1540, 1450, 1340, 1260, 740, 700 | 0.94(3H, d, J=7), 0.98(3H, d, J=7), 1.80-2.20(6H, m), 2.20(3H, m), 2.64(2H, m), 3.20-3.80(4H, m), 5.62(1H, dd, J=9, J=7), 6.26(1H, d, J=9), 7.22(5H, m) |
| 2 (1253) | 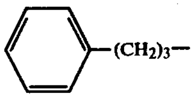 (m = 3) | $-CH_2CH(CH_3)_2$ (n = 1) | 3300, 2950, 2870, 1630, 1530, 1450, 1340, 750, 700 | 0.94(3H, d, J=7), 0.98(3H, d, J=7), 1.40-2.40(11H, m), 2.62(2H, m), 3.20-3.80(4H, m), 5.82(1H, m), 6.19(1H, d, J=9), 7.20(5H, m) |
| 3 (1254) | 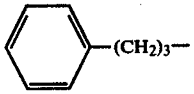 (m = 3) | $-CH_2CH_2-S-CH_3$ (n = 2) | 3300, 2970, 2950, 2875, 1630,1440, 1340, 750, 700 | 1.80-2.80(12H, m), 2.10(3H, s), 3.20-3.80(6H, m), 5.90(1H, m), 6.38(1H, d, J=8), 7.22(5H, m) |
| 4 (1255) | 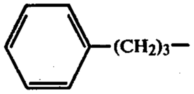 (m = 3) | 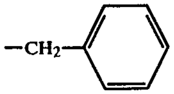 (n = 1) | 3270, 3050, 3020, 2950, 2880, 1660, 1620, 1540, 1440, 1340, 1250, 750, 700 | 1.50-2.30(8H, m), 2.60(3H, m), 3.00(2H, m), 3.36(3H, m), 5.82(1H, m), 6.38(1H, d, J=9), 7.20-7.30(10H, m) |
| 5 (1256) | 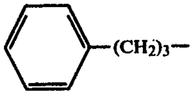 (m = 3) | $-CH_2(CH_2)_2{=}CH_3$ (n = 1) | 3280, 2950, 2930, 2870, 1680, 1440, 740, 700 | 0.88(3H, m), 1.30(4H, m), 1.60-2.40(10H, m), 2.64(2H, m), 3.40(4H, m), 4.74(1H, m), 5.28(1H, d, J=9), 7.21(5H, m), |
| 6 (1261) | 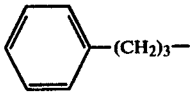 (m = 3) | 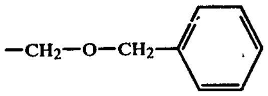 (n = 1) | 3400, 3275, 3050, 2970, 2950, 2875, 1670, 1620, 1540, 1450, 1340, 1230, 1190, 1110, 730, 700 | 1.70-2.40(8H, m), 2.64(2H, m), 3.20-3.80(6H, m), 4.48(2H, m), 4.96(1H, m), 6.44(1H, d, J=8), 7.10-7.40(10H, m) |

TABLE 1-continued
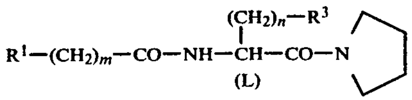
(L)
| Compound No. (SUAM No.) | $R^1-(CH_2)_m-$ | $-(CH_2)_n-R^3$ | IR Spectrum (film, $\nu$ cm$^{-1}$) | NMR Spectrum ($CDCl_3$, $\delta$ ppm) |
|---|---|---|---|---|
| 7 (1268) | 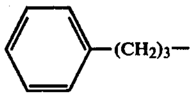 (m = 3) | 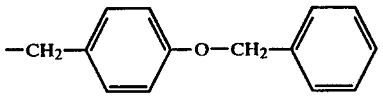 (n = 1) | 3280, 3020, 2950, 2870, 1620, 1500, 1450, 1240, 1170, 1020, 780, 750, 690 | 1.40-2.40(8H, m), 2.60(2H, t, J=8), 2.92(2H, m), 3.32(4H, m), 4.90(1H, m), 5.01(2H, s), 6.60(1H, d, J=8), 6.85(2H, d, J=9), 7.10(2H,d, J=9), 7.20-7.50(10H, m) |
| 8 (1389) | 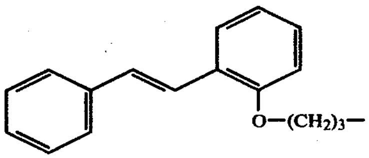 (m = 3) | 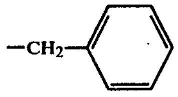 (n = 1) | 3280, 2970, 2870, 1660, 1620, 1530, 1450, 1240, 750 | 1.53(4H, m), 2.05-2.55(4H, m), 2.96(2H, d, J=7.2Hz), 3.28(4H, m), 3.95(2H, t, J=6.0Hz), 4.91(1H, m), 6.68-7.62(12H, m), 7.13(5H, s) |
| 9 (1399) | 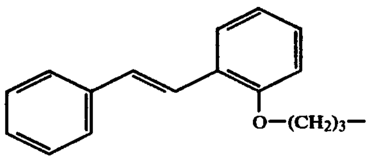 (m = 3) | $-CH_2CH(CH_3)_2$ (n = 1) | 3280, 2940, 2870, 1660, 1620, 1530, 1440, 1230, 750 | 1.87 and 1.93(6H, d, J=6.0Hz), 1.45-2.62(11H, m), 3.22-3.75 (4H, m), 4.00(2H, t, J=6.0Hz), 4.60-4.97(1H, m), 6.70-7.61(12H, m) |
| 10 (1400) | 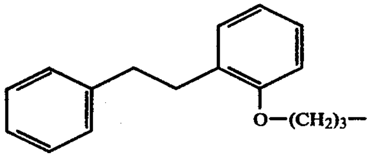 (m = 3) | $-CH(CH_3)_2$ (n = 0) | 3280, 2960, 2870, 1660, 1620, 1530, 1450, 1230, 750 | 1.92(6H, d, J=6.6Hz), 1.63-2.64 (9H, m), 3.28-3.72(4H, m), 4.02(2H, t, J=6.0Hz), 4.57(1H, dd, J=7.2, 9.0Hz), 6.73-7.61(12H, m) |

TABLE 1-continued
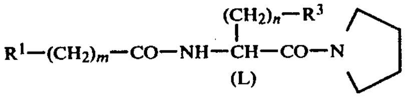
| Compound No. (SUAM No.) | $R^1-(CH_2)_m-$ | $-(CH_2)_n-R^3$ | IR Spectrum (film, $\nu$ $cm^{-1}$) | NMR Spectrum ($CDCl_3$, $\delta$ ppm) |
|---|---|---|---|---|
| 11 (1401) | 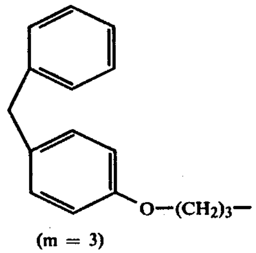 (m = 3) | 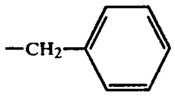 (n = 1) | 3280, 2970, 2870, 1660, 1620, 1530, 1450, 1240, 750, 690 | 1.57(4H, m), 2.07-2.55(4H, m), 2.99(2H, d, J=7.2Hz), 3.30(4H, m), 3.84(2H, s), 3.87(2H, t, J=6.0Hz), 4.93(1H, m), 6.64-7.48(10H, m), 7.16(5H, s) |
| 12 (1402) | 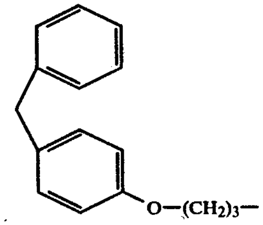 (m = 3) | $-CH_2CH(CH_3)_2$ (n = 1) | 3280, 2950, 2870, 1660, 1620, 1450, 1240 | 1.88, 1.95(3H each, both d, J=6.0Hz), 1.47-2.61(11H, m), 3.27-3.64(4H, m), 3.85(2H, s), 3.90(2H, t, J=6.0Hz), 4.62-4.98(1H, m), 6.65-7.10(4H, m), 7.15(5H, s) |
| 13 (1403) | 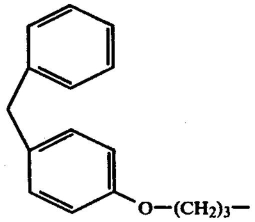 (m = 3) | $-CH(CH_3)_2$ (n = 0) | 3280, 2960, 2870, 1660, 1620, 1530, 1440, 1240 | 1.84(6H, d, J=6.6Hz), 1.62-2.60(9H, m), 3.28-3.67(4H, m), 3.86(2H, s), 3.92(2H, t, J=6.0Hz), 4.57(1H, dd, J=7.2, 8.4Hz), 6.66-7.11(4H, m), 7.16(5H, s) |

TABLE 1-continued
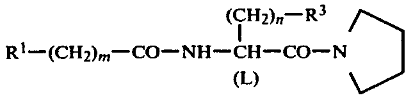
| Compound No. (SUAM No.) | $R^1-(CH_2)_m-$ | $-(CH_2)_n-R^3$ | IR Spectrum (film, $\nu$ $cm^{-1}$) | NMR Spectrum ($CDCl_3$, $\delta$ ppm) |
|---|---|---|---|---|
| 14 (1275) | 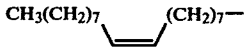 (m = 1) | 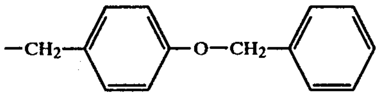 (n = 1) | 3290, 2920, 2850, 1620, 1500, 1445, 1230, 1130, 1020, 730, 690 | 0.88(3H, m), 1.10–2.80(32H, m), 2.92(2H, m), 3.32(4H, m), 4.86(1H, m), 5.02(2H, s), 5.32(2H, m), 6.34(1H, d, J=8), 6.85(2H, d, J=9), 7.10(2H, d, J=9), 7.20–7.50(5H, m) |
| 15 (1283) | 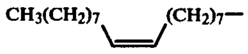 (m = 1) | 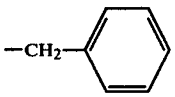 (n = 1) | 3280, 2910, 2850, 1620, 1520, 1440, 740, 690 | 0.87(3H, m), 1.10–2.60(32H, m), 3.00(2H, dd, J=3, J=8), 3.34(4H, m), 4.90(1H, m), 5.32(2H, m), 6.34(1H, d, J=8), 7.21(5H, m) |
| 16 (1284) | 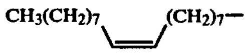 (m = 1) | $-CH_2(CH_2)_2CH_3$ (n = 1) | 3280, 2920, 2850, 1620, 1520, 1440 | 0.88(6H, m), 1.00–2.30(38H, m), 3.30–3.80(4H, m), 4.74(1H, m), 5.32(2H, m), 6.32(1H, d, J=8) |
| 17 (1286) | $CH_3(CH_2)_{16}-$ (m = 1) | 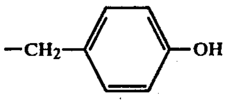 (n = 1) | 3270, 2920, 2850, 1610, 1500, 1445, 1210, 750 | 0.87(3H, m), 1.10–2.80(34H, m), 2.18(2H, t, J=7), 2.90(2H, m), 3.40(4H, m), 4.90(1H, m), 6.42(1H, d, J=9), 6.50(2H, d, J=8), 7.00(2H, d, J=8), 7.16(1H, s) |

TABLE 2
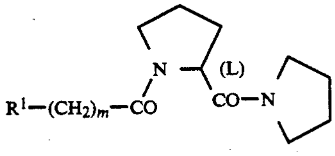
| Compound No. (SUAM No.) | $R^1-(CH_2)_m-$ | IR Spectrum (film, ν $cm^{-1}$) | NMR Spectrum ($CDCl_3$, δ ppm) |
|---|---|---|---|
| 18 (1221) | 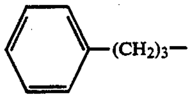 (m = 3) | 2970, 2870, 1640, 1430, 1320, 740, 700 | 1.70-2.47(12H, m), 2.67(2H, m), 3.21-3.90(6H, m), 4.63(1H, m), 7.17(5H, s) |
| 19 (1264) | 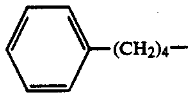 (m = 4) | 2930, 2870, 1630, 1430, 1320, 740, 700 | 1.50-2.78(16H, m), 3.06-3.57(7H, m), 7.16(5H, s) |
| 20 (1258) | 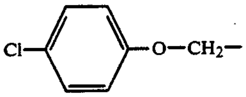 (m = 1) | 3500, 2970, 2875, 1650, 1490, 1440, 1340, 1300, 1230, 1170, 1090, 825, 750, 690 | 1.70-2.40(8H, m), 3.30-4.40(6H, m), 4.64(3H, m), 6.86(2H, d, J=10), 7.22(2H, d, J=10) |
| 21 (1378) | 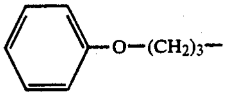 (m = 3) | 2970, 2870, 1630, 1430, 1240, 1030, 750, 690 | 1.83-2.16(12H, m), 3.30-3.78(6H, m), 3.98(2H, t, J=7.2Hz), 4.63(1H, m), 6.74-7.37(5H, m) |
| 22 (1298) | 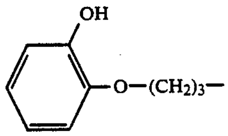 (m = 3) | 2860, 2830, 1620, 1500, 1440, 1100, 1030, 740 | 2.6-3.4(10H, m), 2.53(2H, m), 3.2-4.0(7H, m), 4.10(2H, t), 4.68(1H, m), 6.7-7.0(4H, m) |
| 23 (1371) | 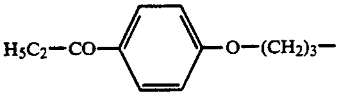 (m = 3) | 2970, 2870, 1640, 1590, 1430, 1250, 1220, 1160, 745 | 1.20(3H, t, J=8), 1.60-2.40(10H, m), 2.52(2H, m), 2.92(2H, q, J=8), 3.10-3.95(6H, m), 4.08(2H, t, J=6), 4.64(1H, m), 6.90(2H, d, J=9), 7.90(2H, d, J=9) |
| 24 (1372) | 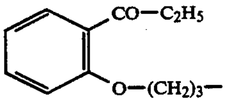 (m = 3) | 2970, 2870, 1640, 1590, 1440, 1340, 1280, 1240, 1200, 750 | 1.16(3H, t, J=7), 1.60-2.40(10H, m), 2.52(2H, m), 2.98(2H, q, J=7), 3.10-3.95(6H, m), 4.12(2H, t, J=6), 4.64(1H, m), 6.80-7.70(4H, m) |
| 25 (1295) | 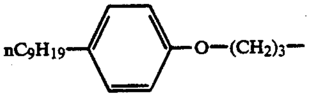 (m = 3) | 2950, 2860, 1630, 1500, 1430, 1240, 1180, 820, 750 | 0.5-2.3(29H, m), 2.52(2H, t), 3.2-3.9(6H, m), 4.00(2H, t), 4.62(1H, m), 6.7-8.2(4H, m) |
| 26 (1294) | 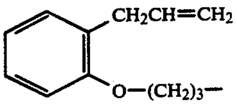 (m = 3) | 2960, 2860, 1630, 1440, 1240, 1140, 750 | 1.7-2.4(10H, m), 2.55(2H, m), 3.3-3.9(8H, m), 4.02(2H, t), 4.68(1H, m), 4.9-5.2(2H, m), 6.00(1H, m), 6.7-7.2(4H, m) |

TABLE 2-continued
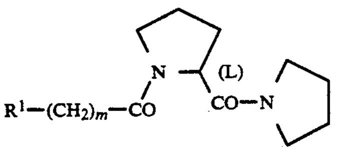
| Compound No. (SUAM No.) | $R^1-(CH_2)_m-$ | IR Spectrum (film, $\nu$ $cm^{-1}$) | NMR Spectrum ($CDCl_3$, $\delta$ ppm) |
|---|---|---|---|
| 27 (1300) | 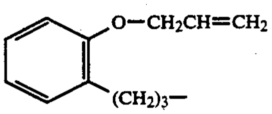 (m = 3) | 2960, 2860, 1630, 1480, 1430, 1230, 740 | 1.7-2.5(12H, m), 2.72(2H, t), 3.2-4.0(6H, m), 4.4-4.8(3H, m), 5.15-5.55(2H, m), 6.10(1H, m), 6.7-7.3(4H, m) |
| 28 (1291) | 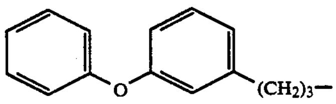 (m = 3) | 2960, 2860, 1640, 1570, 1480, 1430, 1240, 1210, 750, 690 | 1.7-2.5(12H, m), 2.70(2H, t), 3.2-4.0(6H, m), 4.68(1H, m), 6.7-7.5(9H, m) |
| 29 (1299) | 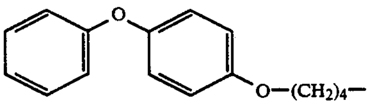 (m = 4) | 2950, 2880, 1640, 1440, 1220, 840, 750 | 1.7-2.5(14H, m), 3.2-4.0(8H, m), 4.60(1H, m), 6.8-7.4(9H, m) |
| 30 (1296) | 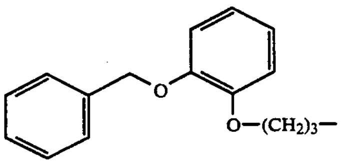 (m = 3) | 2950, 2860, 1630, 1500, 1430, 1250, 1120, 740 | 1.7-2.3(10H, m), 2.4-2.7(2H, m), 3.2-3.9(6H, m), 4.10(2H, t), 4.62(1H, m), 5.10(2H, s), 6.90(4H, s), 7.2-7.5(5H, m) |
| 31 (1369) | 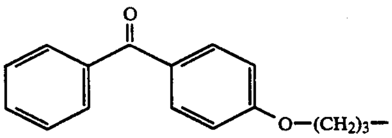 (m = 3) | 2950, 2870, 1640, 1590, 1425, 1310, 1280, 1250, 1165, 920, 740, 700 | 1.60-2.40(10H, m), 2.54(2H, m), 3.20-3.90(6H, m), 4.12(2H, t, J=6), 4.64(1H, m), 6.90-7.85(9H, m) |
| 32 (1370) | 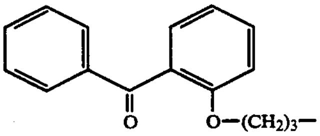 (m = 3) | 2970, 2870, 1640, 1590, 1440, 1310, 1290, 1240, 920, 750, 700, 630 | 1.60-2.40(12H, m), 3.00-3.90(6H, m), 3.96(2H, t, J=6), 4.54(1H, m), 6.90-7.90(9H, m) |
| 33 (1379) | 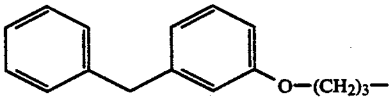 (m = 3) | 2970, 2870, 1640, 1430, 1240, 1100, 1030, 750, 720, 690 | 1.69-2.63(12H, m), 3.25-3.75(6H, m), 3.87(2H, s), 3.96(2H, t, J=7.2Hz), 4.62(1H, m), 6.68-7.12(4H, m), 7.16(5H, s) |
| 34 (1381) | 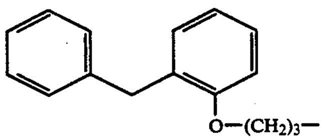 (m = 3) | 2970, 2870, 1640, 1430, 1240, 1100, 1040, 750, 730, 690 | 1.68-2.53(12H, m), 3.14-3.70(6H, m), 3.96(2H, s), 3.96(2H, t, J=7.2Hz), 4.59(1H, m), 6.68-7.44(4H, m), 7.17(5H, s) |

TABLE 2-continued
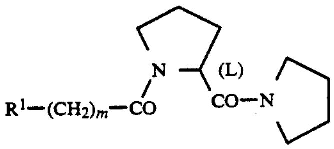
| Compound No. (SUAM No.) | $R^1-(CH_2)_m-$ | IR Spectrum (film, $\nu$ $cm^{-1}$) | NMR Spectrum ($CDCl_3$, $\delta$ ppm) |
|---|---|---|---|
| 35 (1289) | 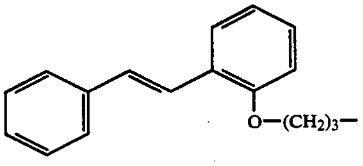 (m = 3) | 3000, 2900, 1680, 1450, 1250, 760 | 1.7-2.4(10H, m), 2.60(2H, m), 3.2-3.9(8H, m), 4.1(2H, t), 4.6(1H, m), 6.8-7.6(11H, m) |
| 36 (1290) | 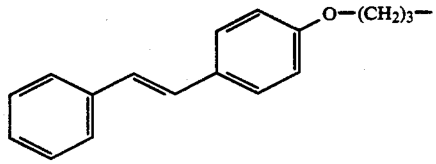 (m = 3) | 2950, 2860, 1630, 1500, 1430, 1240, 1170, 820, 740, 690 | 1.8-2.4(10H, m), 2.54(2H, t), 3.3-3.9(6H, m), 4.05(2H, t), 4.66(1H, m), 6.8-7.7(11H, m) |
| 37 (1293) | 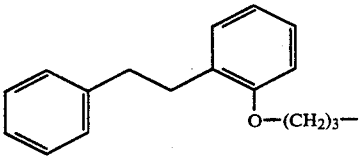 (m = 3) | 2980, 2890, 1640, 1500, 1450, 1250, 1050, 750 | 1.7-2.3(10H, m), 2.55(2H, m), 2.90(4H, s), 3.2-3.9(6H, m), 4.05(2H, t), 4.65(1H, m), 6.7-7.3(9H, m) |
| 38 (1456) | 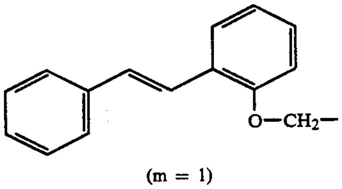 (m = 1) | 3050, 2970, 2880, 1640, 1440, 1230, 760, 690 | 1.78-2.40(8H, m), 3.20-3.96(6H, m), 4.76(2H, s), 4.68(1H, m), 6.84-7.64(11H, m) |
| 39 (1457) | 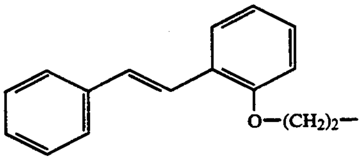 (m = 2) | 3050, 2970, 2870, 1640, 1440, 1240, 760, 690 | 1.80-2.32(8H, m), 2.91(2H, m), 3.28-3.93(6H, m), 4.40(2H, m), 4.66(1H, m), 6.92-7.62(11H, m) |
| 40 (1458) | 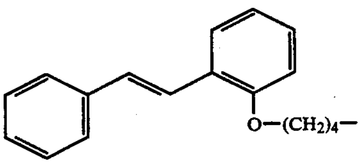 (m = 4) | 3050, 2950, 2860, 1640, 1430, 1230, 750, 690 | 1.72-2.26(12H, m), 2.43(2H, m), 3.28-3.88(6H, m), 4.05(2H, m), 4.62(1H, m), 6.84-7.62(11H, m) |
| 41 (1383) | 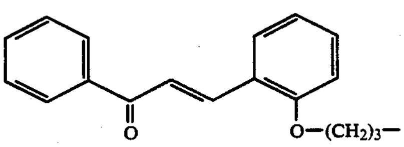 (m = 3) | 2970, 2870, 1630, 1590, 1430, 1330, 1270, 1240, 1210, 1030, 1010, 750, 690 | 1.69-2.70(12H, m), 3.20-3.72(6H, m), 4.11(2H, t, J=7.2Hz), 4.60(1H, m), 6.75-7.02(2H, m), 7.16-8.22(9H, m) |

TABLE 2-continued

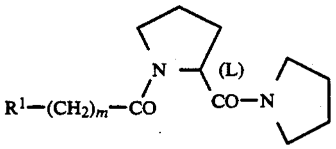

| Compound No. (SUAM No.) | $R^1-(CH_2)_m-$ | IR Spectrum (film, ν $cm^{-1}$) | NMR Spectrum ($CDCl_3$, δ ppm) |
|---|---|---|---|
| 42 (1384) | 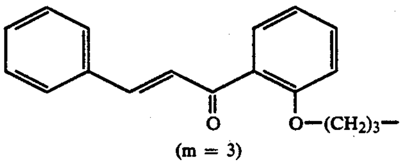 (m = 3) | 2970, 2870, 1640, 1590, 1430, 1320, 1240, 1200, 1020, 1010, 750, 690 | 1.70-2.55(12H, m), 3.20-3.78(6H, m), 4.12(2H, t, J=7.2Hz), 4.52(1H, m), 6.83-7.07(2H, m), 7.18-7.77(9H, m) |
| 43 (1280) | 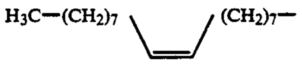 (m = 1) | 2920, 2850, 1640, 1430, 1340, 1320, 750 | 0.86(3H, m), 1.00-2.40(36H, m), 3.20-4.00(6H, m), 4.64(1H, m), 5.32(2H, m) |
| 44 (1391) | $n-C_{15}H_{31}-$ (m = 1) | 2940, 2870, 1650, 1440, 1345, 1330, 760 | 0.88(3H, m), 1.26(26H, m), 1.40-2.40(10H, m), 3.30-4.00(6H, m), 4.64(1H, m) |
| 45 (1392) | $n-C_{11}H_{23}-$ (m = 1) | 2950, 2880, 1650, 1440, 1350, 1335, 760 | 0.88(3H, m), 1.26(18H, m), 2.40-3.40(10H, m), 3.20-4.00(6H, m), 4.66(1H, m) |
| 46 (1393) | 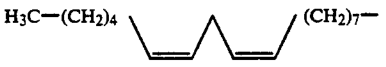 (m = 1) | 2930, 2850, 1650, 1430, 1340, 1320, 750 | 0.86(3H, m), 1.28(16H, m), 1.40-2.40(14H, m), 2.72(2H, m), 3.20-4.00(6H, m), 4.64(1H, m), 5.32(4H, m) |

EXPERIMENT 1

Measurement of anti-prolyl endopeptidase activity

The method of Yoshimoto and Tsuru [T. Yoshimoto and D. Tsuru, Agric. Biol. Chem., 42, 2417 (1978)] was used to measure the anti-prolyl endopeptidase activities of several compounds of the present invention. A mixture of 0.0025M Z-glycyl-proline-β-naphthylamide (0.25 ml), 0.1M phosphate buffer (pH, 7.0; 0.99 ml) and a solution of a particular anti-propyl endopeptidase compound (0.01 ml) was incubated in a test tube at 37° C. for 3 minutes. Thereafter, 0.1 ml of a solution of prolyl endopeptidase (0.2 U/ml) was added and the mixture was incubated at 35° C. for 10 minutes. After the reaction, 2.0 ml of Triton X-100 in 1M acetate buffer (pH, 4.0) was added to the reaction mixture so that the final concentration of the surfactant was 10%. The mixture was left at room temperature for 15 minutes and the absorbance (a) at 410 nm was measured.

A sample of a blind test was prepared by using the buffer instead of the anti-prolyl endopeptidase compound and its absorbance (b) was also measured. The percent inhibition of prolyl endopeptidase was calculated by the formula:

$$[(b-a)/b]\times 100$$

and the amount of a specific compound needed to achieve 50% inhibition ($IC_{50}$) was determined. The results are shown in Table 3.

TABLE 3

| Compound No. | (SUAM No.) | $IC_{50}$ (μg/test tube) |
|---|---|---|
| 2 | (1253) | 0.15 |
| 5 | (1256) | 0.15 |
| 9 | (1399) | 0.03 |
| 10 | (1400) | 0.02 |
| 12 | (1402) | 0.08 |
| 13 | (1403) | 0.04 |
| 16 | (1284) | 0.07 |
| 18 | (1221) | 0.02 |
| 20 | (1258) | 0.20 |
| 21 | (1378) | 0.001 |
| 22 | (1298) | 0.008 |
| 23 | (1371) | 0.003 |
| 24 | (1372) | 0.004 |
| 25 | (1295) | 0.008 |
| 26 | (1294) | 0.002 |
| 27 | (1300) | 0.01 |
| 29 | (1299) | 0.009 |
| 30 | (1296) | 0.005 |
| 31 | (1369) | 0.004 |
| 32 | (1370) | 0.001 |
| 33 | (1379) | 0.0004 |
| 34 | (1381) | 0.001 |
| 35 | (1289) | 0.001 |
| 36 | (1290) | 0.003 |
| 37 | (1293) | 0.002 |
| 39 | (1457) | 0.003 |
| 40 | (1458) | 0.002 |
| 41 | (1383) | 0.001 |
| 42 | (1384) | 0.0008 |
| 43 | (1280) | 0.02 |
| 46 | (1393) | 0.015 |

EXPERIMENT 2

Measurement of preventive effect against experimental amnesia caused in rats by scopolamine (Intraperitoneal administration)

Several of the anti-prolyl endopeptidase compounds according to the present invention were checked for their ability to prevent the inhibition of long-term memory fixation by scopolamine. Solutions of physiological saline which contained 25 mg/kg or 5 mg/kg of selected compound of the present invention were administered intraperitoneally once a day to Wister male rats (100 to 120 g). One hour after the administration, electric shocks were applied to the rats so that they would acquire passive avoidance learning. Immediately thereafter, scopolamine was administered intraperitoneally to each rat in an amount of 3 mg per kg of body weight.

The results of the test were assessed 24 hours after the administration of scopolamine. The number of amnesic rats and of sound rats was counted for each of the control group (rats to which the test compounds were not administered but to which only scopolamine and physiological saline were administered intraperitoneally) and the treated group (rats to which both the test compound and scopolamine were administered). The results are shown in Table 4.

TABLE 5-continued

| Compound No. | (SUAM No.) | $LD_{50}$ (mg/kg) |
|---|---|---|
| 42 | (1384) | 360 |

The present invention includes pharmaceutical compositions which contain compounds according to the present invention which are effective for the treatment of symptoms caused by organic disorders of the brain together with adjuvants which are acceptable from the pharmaceutical point of view.

These active ingredients and pharmaceutical compositions are administered orally in suitable solid forms such as capsules, tablets and powders, or liquid forms such as elixir, syrup and suspensions. They may also be administered parenterally, e.g., in the form of injections or suppositories.

As an example of suitable excipients for solid drugs which are contained in drug components, a carrier in solid powder form may be cited such as lactose, saccharose, mannitol, sorbitol, cellulose and glycine.

As an example of suitable lubricants, silicon dioxide, talc, magnesium stearate and polyethylene glycol may be cited, while starch, gelatin, tragacanth, methyl cellulose, sodium carboxymethyl cellulose and polyvinyl pyrrolidone may be cited as binders. Starch or agar may be used as a disintegrator.

The compounds according to the present invention are orally administered in a daily dose of 10 to 2,000 mg, preferably, 100 to 1,000 mg per adult. Alternatively, they may be administered parenterally in a dose of 1 to 1,000 mg, preferably, 50 to 500 mg. It is understood that the dosage will differ depending upon the symptoms of the disease, the age and weight of a patient, the stage of the symptoms and the form of administration.

TABLE 4

| | | Amnesia test with rats (intraperitoneal administration) | | | | | | |
|---|---|---|---|---|---|---|---|---|
| | | | Learning | | | | Pharmacological effects | |
| Compound No. (SUAM No.) | Drug administration after learning | No. of rats tested | Initial avoidance time (sec.) | No. of avoidances during learning | Learning time (sec.) | Avoidance time (sec.) After 24 hrs | No. of amnesic rats/No. of rats tested | Percentage amnesia |
| physiological saline | physiological saline | 10 | 3.5 | 1.6 | 110 | 173.8 | 5/10 | 50 |
| physiological saline | scopolamine (3 mg/kg i.p.) | 10 | 1.7 | 2.2 | 110 | 37.6 | 10/10 | 100 |
| 1 (1252) (25 mg/kg i.p.) | scopolamine (3 mg/kg i.p.) | 10 | 2.4 | 1.8 | 110 | 243.0 | 3/10 | 30 |
| 2 (1253) (25 mg/kg i.p.) | scopolamine (3 mg/kg i.p.) | 10 | 2.7 | 2.2 | 110 | 264.6 | 2/10 | 20 |
| 16 (1284) (20 mg/kg i.p.) | scopolamine (3 mg/kg i.p.) | 10 | 2.2 | 2.1 | 110 | 252.0 | 2/10 | 20 |
| 18 (1221) (5 mg/kg i.p.) | scopolamine (3 mg/kg i.p.) | 10 | 2.8 | 1.8 | 110 | 300.0 | 0/10 | 0 |
| 43 (1280) (1 mg/kg i.p.) | scopolamine (3 mg/kg i.p.) | 10 | 1.9 | 3.4 | 110 | 240.8 | 2/10 | 20 |

EXPERIMENT 3

Acute toxicity test in mice

The compounds of the present invention were checked for their acute toxicity in ($LD_{50}$) CDF-1 strain male mice (body weight: 27.2 to 30.1 g).

Test samples were prepared by dissolving the respective compounds in DMSO, and a portion (0.1 ml) of the so conditioned test sample was administered intraperitoneally to each of the mice used. Each of the treated groups consisted of five mice. The results of this test are shown in Table 5.

TABLE 5

| Compound No. | (SUAM No.) | $LD_{50}$ (mg/kg) |
|---|---|---|
| 2 | (1253) | >600 |
| 21 | (1384) | 350 |
| 26 | (1294) | 390 |
| 27 | (1300) | 390 |
| 37 | (1293) | 350 |

| Formulation 1 | |
|---|---|
| active substance (Compound No. 18) | 10 parts |
| lactose | 75 parts |
| heavy magnesium oxide | 15 parts |

These components were uniformly mixed and formed into powders or granules.

| Formulation 2 | |
|---|---|
| active substance (Compound No. 18) | 45 parts |
| starch | 15 parts |
| lactose | 40 parts |

These components were uniformly mixed and formed into tablets or capsules.

| Formulation 3 | |
|---|---|
| active substance (Compound No. 18) | 1 part |
| surfactant | 5 parts |
| physiological saline | 94 parts |

These components were mixed under warming and were sterilized to obtain injections.

As described above, the compounds according to the present invention exhibit appreciable anti-prolyl endopeptidase activity and anti-amnesic effects. The acute toxicity test results show that the compounds cause little toxicity. Because of this relatively wide margin of safety as compared with their remarkable anti-prolyl endopeptidase activity, the compounds of the present invention hold promise as pharmaceuticals for preventing and curing amnesia.

What is claimed is:

1. Pyrrolidineamide derivatives of acylamino acid of the general formula:

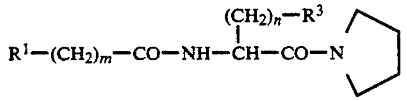

wherein m is an integer of 1 to 3;

n is 0, 1 or 2;

$R^1$ is phenyl, phenoxy, mono-substituted-phenyl or -phenoxy wherein the substituents on the substituted-phenyl or -phenoxy are selected from the group consisting of halogen, hydroxy, phenylalkyl having 7 to 10 carbon atoms, styryl, phenoxy, benzoyl and benzyloxy; a straight alkyl having 10 to 16 carbon atoms; or a straight alkenyl having 10 to 16 carbon atoms;

$R^3$ is H, $NH_2$, OH, $SCH_3$, carboxyl, a straight or branched ($C_3$-$C_5$)alkyl, phenyl, benzyloxy, benzyloxyphenyl, indolyl, or imidazolyl.

2. A pharmaceutical composition for use in ameliorating cerebral insufficiency which comprises as an active ingredient a pharmaceutically effective amount of a compound of the general formula:

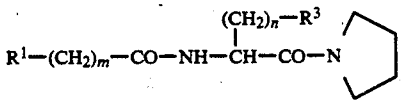

wherein m is an integer of 1 to 3;

n is 0, 1 or 2;

$R^1$ is phenyl, phenoxy, mono-substituted-phenyl or -phenoxy wherein the substituents on the substituted -phenyl or -phenoxy are selected from the group consisting of halogen, hydroxy, phenylalkyl having 7 to 10 carbon atoms, styryl, phenoxy, benzoyl and benzyloxy; a straight alkyl having 10 to 16 carbon atoms; or a straight alkenyl having 10 to 16 carbon atoms;

$R^3$ is H, $NH_2$, OH, $SCH_3$, carboxyl, a straight or branched ($C_3$-$C_5$)alkyl, phenyl, benzyloxy, benzyloxyphenyl, indolyl, or imidazolyl, together with a pharmaceutical acceptable carrier.

3. A pharmaceutical composition according to claim 2 wherein said composition contains the active ingredient in an amount effective for ameliorating amnesia.

4. A pharmaceutical composition according to claim 2 wherein the active ingredient is contained in an amount of 10 to 2,000 mg in a daily dose.

* * * * *